(12) United States Patent
Koyanagi et al.

(10) Patent No.: US 7,994,201 B2
(45) Date of Patent: *Aug. 9, 2011

(54) ANTHRANILAMIDE COMPOUNDS, PROCESS FOR THEIR PRODUCTION AND PESTICIDES CONTAINING THEM

(75) Inventors: Toru Koyanagi, Kusatsu (JP); Masayuki Morita, Kusatsu (JP); Kenichi Nakamoto, Kusatsu (JP); Akihiro Hisamatsu, Kusatsu (JP)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/552,077

(22) Filed: Sep. 1, 2009

(65) Prior Publication Data

US 2010/0035935 A1     Feb. 11, 2010

Related U.S. Application Data

(63) Continuation of application No. 10/589,782, filed as application No. PCT/JP2005/002351 on Feb. 16, 2005, now Pat. No. 7,612,100.

(30) Foreign Application Priority Data

| Feb. 18, 2004 | (JP) | ................................ | 2004-041295 |
| Apr. 28, 2004 | (JP) | ................................ | 2004-133722 |
| Sep. 8, 2004 | (JP) | ................................ | 2004-261507 |
| Oct. 8, 2004 | (JP) | ................................ | 2004-295778 |

(51) Int. Cl.
    *A01N 43/40* (2006.01)
(52) U.S. Cl. ........................ 514/341; 424/405
(58) Field of Classification Search ............ 514/341
    See application file for complete search history.

(56) References Cited

U.S. PATENT DOCUMENTS

| 6,559,341 | B2 | 5/2003 | Tohnishi et al. |
| 6,747,047 | B2 | 6/2004 | Lahm et al. |
| 6,995,178 | B2 | 2/2006 | Lahm et al. |
| 7,199,138 | B2 * | 4/2007 | Finkelstein et al. .......... 514/341 |
| 7,232,836 | B2 | 6/2007 | Lahm et al. |
| 7,247,647 | B2 | 7/2007 | Hughes et al. |
| 7,338,978 | B2 | 3/2008 | Lahm et al. |
| 7,612,100 | B2 | 11/2009 | Koyanagi et al. |
| 2003/0055287 | A1 | 3/2003 | Tohnishi et al. |
| 2003/0229050 | A1 | 12/2003 | Lahm et al. |
| 2004/0142984 | A1 | 7/2004 | Lahm et al. |
| 2004/0198984 | A1 | 10/2004 | Lahm et al. |
| 2004/0209923 | A1 | 10/2004 | Berger et al. |
| 2004/0254237 | A1 | 12/2004 | Nakamura et al. |
| 2005/0075372 | A1 | 4/2005 | Lahm et al. |
| 2006/0079561 | A1 | 4/2006 | Lahm et al. |
| 2006/0111403 | A1 | 5/2006 | Hughes et al. |
| 2007/0225336 | A1 | 9/2007 | Lahm et al. |
| 2007/0264299 | A1 | 11/2007 | Hughes et al. |
| 2008/0275061 | A1 | 11/2008 | Lahm et al. |
| 2008/0275065 | A1 | 11/2008 | O'Sullivan et al. |
| 2009/0133318 | A1 | 5/2009 | Lahm |

FOREIGN PATENT DOCUMENTS

| JP | 11-240857 A | 9/1999 |
| JP | 2003-176258 A | 6/2003 |
| JP | 2003-528070 A | 9/2003 |
| WO | 01/70671 A2 | 9/2001 |
| WO | 03/015518 A1 | 2/2003 |
| WO | 03/015519 A1 | 2/2003 |
| WO | 03/024222 A1 | 3/2003 |
| WO | 2004/067528 A1 | 8/2004 |
| WO | 2006/040113 A2 | 4/2006 |
| WO | 2006/055922 A2 | 5/2006 |

OTHER PUBLICATIONS

Coppola, "The Chemistry of Isatoic Anhydride", Department of Medicinal Chemistry, Pharmaceutical Division, Sandoz Inc., pp. 505-536, 1980.

Katritzky et al., "Synthesis of 1-Hydroxy-7-Phenoxynaphthalene", Center for Heterocyclic Compounds, Corporate Research Science Laboratory, vol. 25, No. 5, pp. 585-590, 1993.

* cited by examiner

*Primary Examiner* — Neil Levy

(74) *Attorney, Agent, or Firm* — Greenblum & Bernstein, P.L.C.

(57) ABSTRACT

Anthranilamide compounds, a process for their production, and pesticides containing these compounds as active ingredients. This Abstract is not intended to define the invention disclosed in the specification, nor intended to limit the scope of the invention in any way.

4 Claims, No Drawings

ANTHRANILAMIDE COMPOUNDS, PROCESS FOR THEIR PRODUCTION AND PESTICIDES CONTAINING THEM

CROSS-REFERENCE TO RELATED APPLICATIONS

The present application is a continuation of U.S. application Ser. No. 10/589,782 filed Aug. 17, 2006 now U.S. Pat. No. 7,612,100, which is a National Stage of International Application PCT/JP05/02351, filed Feb. 16, 2005, the disclosures of which are expressly incorporated by reference herein in their entireties.

TECHNICAL FIELD

Patent Documents 1, 2, 3 and 4, respectively, disclose anthranilamide compounds having certain specific chemical structures. However, none of these Patent Documents discloses compounds having alkyl substituted by $C_{3-4}$ cycloalkyl as a substituent corresponding to A in the compounds of formula (I) of the present invention.

Further, Patent Document 5 discloses anthranilamide compounds having a cyano group at the 4-position of the benzene ring. However, a cyano group is not contained in the definition of $R^1$ in the after-mentioned formula (I) of the present invention, and the respective chemical structures are different.

Patent Document 1: International Publication WO03/24222

Patent Document 2: International Publication WO03/15518

Patent Document 3: International Publication WO03/15519

Patent Document 4: International Publication WO01/70671

Patent Document 5: International Publication

DISCLOSURE OF THE INVENTION

Problems to be Solved by the Invention

For many years, many pesticides have been used, but many of them have various problems such that the effects are inadequate, their use is restricted as pests have acquired resistance, etc. Accordingly, it is desired to develop a novel pesticide substantially free from such problems, for example, a pesticide capable of controlling various pests which create problems in agricultural and horticultural fields or a pesticide which is capable of controlling pests parasitic on animals.

Means to Solve the Problems

The present inventors have conducted various studies on anthranilamide compounds in an effort to find a superior pesticide. As a result, they have found that a novel anthranilamide compound or its salt has an extremely high pesticidal effect against pests at a low dose and have accomplished the present invention. Namely, the present invention relates to an anthranilamide compound represented by the formula (I) or its salt:

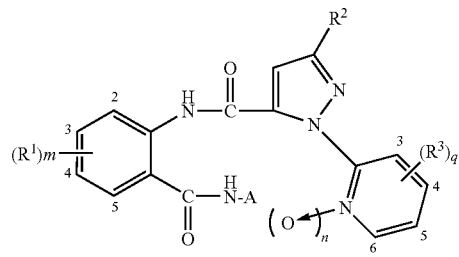

wherein $R^1$ is halogen, alkyl, haloalkyl, alkenyl, haloalkenyl, alkynyl, haloalkynyl, alkoxy, haloalkoxy, alkylcarbonyl, haloalkylcarbonyl, alkoxycarbonyl, haloalkoxycarbonyl, phenoxycarbonyl which may be substituted, nitro or formyl; each of $R^2$ and $R^3$ which are independent of each other, is halogen, alkyl, haloalkyl, alkoxy, haloalkoxy or cyano; A is alkyl substituted by Y; Y is $C_{3-4}$ cycloalkyl which may be substituted by at least one substituent selected from the group consisting of halogen, alkyl and haloalkyl; m is from 0 to 4; n is 0 or 1; and q is from 0 to 4; provided that when $R^1$ is a fluorine atom, a chlorine atom, a bromine atom or methyl substituted at the 2-position of the benzene ring and another $R^1$ is halogen substituted at the 4-position of the benzene ring, the halogen at the 4-position is a fluorine atom or a chlorine atom; a process for its production; and a pesticide containing it.

Effects of the Invention

The pesticide containing, as an active ingredient, the novel anthranilamide compound represented by the above formula (I), has a very high pesticidal effect against pests at a low dose.

BEST MODE FOR CARRYING OUT THE INVENTION

The substituents for the phenoxycarbonyl which may be substituted, in $R^1$, may, for example, be halogen, alkyl, haloalkyl, alkoxy, haloalkoxy, alkylthio, haloalkylthio, alkylsulfinyl, haloalkylsulfinyl, alkylsulfonyl, haloalkylsulfonyl, cyano and nitro. The number of such substituents may be 1 or more, and if more, the respective substituents may be the same or different. Further, the positions for substitution for the respective substituents may be any positions.

The number of substituents Y in A may be 1 or more, and if more, the respective substituents Y may be the same or different. Further, the positions for substitution of the substituents Y may be any positions The number of substituents Y in A is preferably 1.

The number of halogen, alkyl or haloalkyl as the substituent for the $C_{3-4}$ cycloalkyl in Y, may be 1 or more, and if more, the respective substituents may be the same or different. Further, the positions for substitution for the respective substituents may be any positions. The $C_{3-4}$ cycloalkyl in Y is preferably unsubstituted, or when it has the above substituents, the number of such substituents is preferably from 1 to 5.

As the halogen or halogen as the substituent in $R^1$, $R^2$, $R^3$ or Y, an atom of fluorine, chlorine, bromine or iodine may be mentioned. The number of halogens as substituents may be 1 or more, and if more, the respective halogens may be the same or different. Further, the positions for substitution of such halogens may be any positions.

The alkyl or alkyl moiety in $R^1$, $R^2$, $R^3$, A or Y may be linear or branched. As its specific example, $C_{1-6}$ alkyl such as methyl, ethyl, propyl, isopropyl, butyl, tert-butyl, pentyl or hexyl may be mentioned.

The alkenyl or alkenyl moiety in $R^1$ may be linear or branched. As its specific example, $C_{2-6}$ alkenyl such as vinyl, 1-propenyl, allyl, isopropenyl, 1-butenyl, 1,3-butadienyl or 1-hexenyl may be mentioned.

The alkynyl or alkynyl moiety in $R^1$ may be linear or branched. As its specific example, $C_{2-6}$ alkynyl such as ethynyl, 2-butynyl, 2-pentynyl or 3-hexynyl may be mentioned.

As a specific example of the $C_{3-4}$ cycloalkyl or cycloalkyl moiety in Y, cyclopropyl or cyclobutyl may be mentioned, and cyclopropyl is particularly preferred.

The salt of the anthranilamide compound of the above formula (I) includes all kinds so long as they are agriculturally acceptable. For example, an alkali metal salt such as a sodium salt or a potassium salt; an alkaline earth metal salt such as a magnesium salt or a calcium salt; an ammonium salt such as a dimethylammonium salt or a triethylammonium salt; an inorganic acid salt such as a hydrochloride, a perchlorate, a sulfate or a nitrate; or an organic acid salt such as an acetate or a methanesulfonate, may be mentioned.

The anthranilamide compound of the formula (I) may have optical isomers or geometrical isomers, and such isomers and mixtures thereof are both included in the present invention. Further, in the present invention, various isomers other than those mentioned above, may be included within the scope of the common knowledge in this technical field. Further, depending upon the type of such an isomer, the chemical structure may be different from the above-mentioned formula (I), but it is obvious to one skilled in the art that such a structure is in isomeric relation and thus falls within the scope of the is present invention.

The anthranilamide compound of the above formula (I) or its salt (hereinafter referred to simply of the compound of the present invention) can be produced by the following reactions (A) and (B) and in accordance with a usual method for producing a salt.

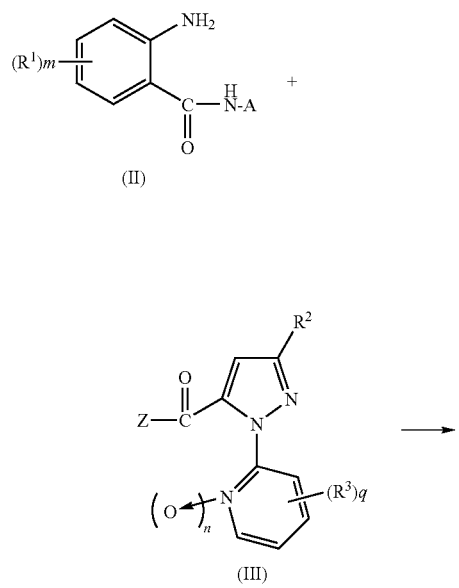

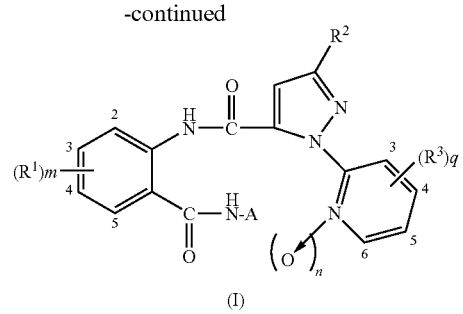

$R^1$, $R^2$, $R^3$, A, m, n and q are as defined above, and Z is a chlorine atom, —OH or $C_{1-4}$ alkoxy.

In a case where Z is a chlorine atom, the reaction (A) can be carried out usually in the presence of a base.

As the base, one or more types may suitably be selected for use from, for example, an alkali metal hydroxide such as sodium hydroxide or potassium hydroxide; an alkali metal carbonate such as sodium carbonate or potassium carbonate; an alkali metal hydride such as sodium hydride or potassium hydride; and a tertiary amine such as trimethylamine, triethylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene or 1,4-diazabicyclo2.2.2octane. The base may be used in an amount of from 1 to 5 times by mol, preferably from 1 to 2.5 times by mol, to the compound of the formula (II).

In a case where Z is a chlorine atom, the reaction (A) can be carried out in the presence of a solvent, as the case requires. The solvent may be any solvent so long as it is a solvent inert to the reaction. For example, one or more types may suitably be selected for use from, for example, an ether such as diethyl ether, butyl ethyl ether, tetrahydrofuran, dioxane or dimethoxyethane; a halogenated hydrocarbon such as chlorobenzene, dichlorobenzene, dichloromethane, chloroform, carbon tetrachloride, dichloroethane, trichloroethane or dichloroethylene; an aromatic hydrocarbon such as benzene, toluene or xylene; a dipolar aprotic solvent such as acetonitrile, propionitrile, N,N-dimethylformamide, dimethylsufoxide, hexamethylphosphoric triamide, sulfolane, dimethylacetamide or N-methylpyrrolidone; an ester such as methyl acetate, ethyl acetate or propyl acetate; and a ketone such as acetone, diethyl ketone, methyl ethyl ketone or methyl isobutyl ketone.

In a case where Z is a chlorine atom, the reaction (A) can be carried out usually from −20 to +60° C., preferably from 0 to 30° C. The reaction time is usually from about 1 to 24 hours, preferably from about 2 to 12 hours.

In a case where Z is —OH, the reaction (A) can be carried out usually in the presence of a dehydration condensing agent and a solvent.

The dehydration condensing agent may, for example, be a carbodiimide such as N,N'-dicyclohexylcarbodiimide, 1,3-diisopropylcarbodiimide or 1-ethyl-3-(3-dimethylaminopropyl)carbodiimide hydrochloride; or others such as 1,1'-carbonyl-bis-1H-imidazole, phenyl Cdichlorophosphate, diethyl phosphorocyanidate, 1,3,5-triaza-2,4,6-triphosphorin-2,2,4,4,6,6-hexachloride, cyanuric chloride, isobutyl chloroformate, chlorosulfonyl isocyanate, or trifluoroacetic anhydride.

The solvent may be any solvent so long as it is inert to the reaction. For example, one or more types may suitably be selected for use from, for example, an ether such as diethyl ether, butyl ethyl ether, tetrahydrofuran, dioxane or dimethoxyethane; a halogenated hydrocarbon such as chlorobenzene, dichlorobenzene, dichloromethane, chloroform, carbon tetrachloride, dichloroethane, trichloroethane or dichloroethylene; an aromatic hydrocarbon such as benzene, toluene or xylene; a dipolar aprotic solvent such as acetonitrile, propionitrile, N,N-dimethylformamide, dimethylsufoxide, hexamethylphosphoric triamide, sulfolane, dimethylacetamide or N-methylpyrrolidone; an ester such as methyl acetate, ethyl acetate or propyl acetate; a ketone such as acetone, diethyl ketone, methyl ethyl ketone or methyl isobutyl ketone; and a aliphatic hydrocarbon such as pentane, hexane, heptane, octane or cyclohexane.

In a case where Z is —OH, the reaction (A) can be carried out usually from −20 to +60° C., preferably from 0 to 30° C. The reaction time is usually from about 0.5 to 24 hours, preferably from about 1 to 12 hours.

In a case where Z is $C_{1-4}$ alkoxy, the reaction (A) can be carried out usually in the presence of a base and a solvent. As the base, one or more types may suitably be selected for use from, for example, an alkali metal hydride such as sodium hydride or potassium hydride; an alkali metal alkoxide such as sodium methoxide, sodium ethoxide or potassium tertiary butoxide; and a tertiary amine such as trimethylamine, triethylamine, triisopropylamine, diisopropylethylamine, pyridine, 4-dimethylaminopyridine, 2,6-dimethylpyridine, 4-pyrrolidinopyridine, N-methyl morpholine, N,N-dimethylaniline, N,N-diethylaniline, N-ethyl-N-methylaniline, 1,8-diazabicyclo[5.4.0]-7-undecene or 1,4-diazabicyclo[2.2.2]octane. The base may be used in an amount of from 1 to 5 times by mol, preferably from 1 to 2.5 times by mol, to the compound of the formula (II).

The solvent may be any solvent so long as it is inert to the reaction. For example, one or more types may suitably be selected for use from, for example, an ether such as diethyl ether, butyl ethyl ether, tetrahydrofuran, dioxane or dimethoxyethane; an aromatic hydrocarbon such as benzene, toluene or xylene; a dipolar aprotic solvent such as acetonitrile, propionitrile, N,N-dimethylformamide, dimethylsufoxide, hexamethylphosphoric triamide, sulfolane, dimethylacetamide or N-methylpyrrolidone and an alcohol such as methanol, ethanol, propanol, n-butanol or tert-butanol.

In a case where Z is $C_{1-4}$ alkoxy, the reaction (A) can be carried out usually from 0 to 120° C., preferably from 20 to 80° C. The reaction time is usually from about 0.5 to 24 hours, preferably from about 1 to 12 hours.

The compound of the above formula (II) or (III) may be a known compound or may be produced in accordance with known reference materials. For example, the compound of the formula (II) can be produced by or in accordance with the method disclosed in Synthesis, 1980, p. 505. The compound of the formula (III) can be produced by or in accordance with the method disclosed in schemes 9 to 22 in WO03/24222.

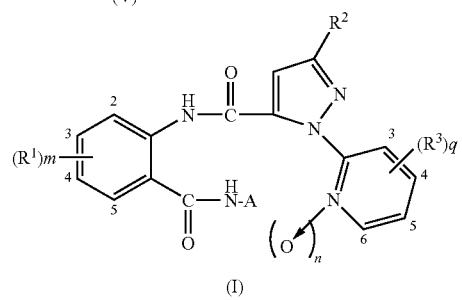

$R^1$, $R^2$, $R^3$, A, m, n and q are as defined above.

The reaction (B) can be carried out usually in the presence of a solvent.

The solvent may be any solvent so long as it is inert to the reaction. For example, one or more types may suitably be selected for use from, for example, an ether such as diethyl ether, butyl ethyl ether, tetrahydrofuran, dioxane or dimethoxyethane; a halogenated hydrocarbon such as chlorobenzene, dichlorobenzene, dichloromethane, chloroform, carbon tetrachloride, dichloroethane, trichloroethane or dichloroethylene; an aromatic hydrocarbon such as benzene, toluene or xylene; and a dipolar aprotic solvent such as acetonitrile, propionitrile, N,N-dimethylformamide, dimethylsufoxide, hexamethylphosphoric triamide, sulfolane, dimethylacetamide or N-methylpyrrolidone.

The reaction (B) can be carried out usually from 0 to 120° C., preferably from 20 to 80° C. The reaction time is usually about from 0.5 to 24 hours, preferably from about 1 to 12 hours.

The compound of the above formula (IV) may be a known compound or may be produced in accordance with a known reference material. For example, the compound of the formula (IV) can be produced by or in accordance with the method disclosed in Org. Prep. Proceed. Int., 1993, vol. 25, p. 585 or the method disclosed in schemes 8 to 10 in WO03/24222.

The compound of the above formula (V) includes a novel compound. Such a compound can be produced by the Gabriel method, and can be produced, for example, in accordance with the following reaction (C).

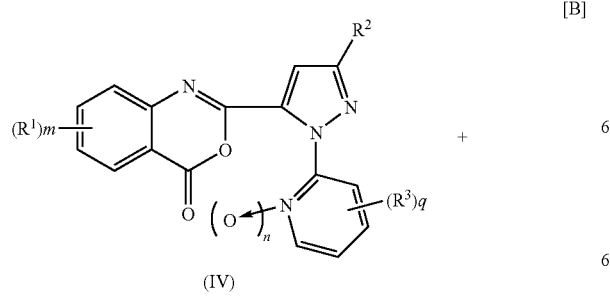

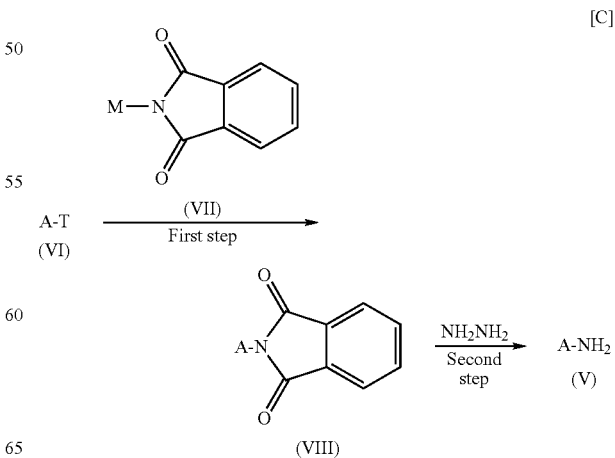

In the reaction (C), A is as defined above, and T is halogen, —OSO$_2$G (G is a sulfonate residue) or —OH. When T is halogen or —OSO$_2$G, M is sodium or potassium, and when T is —OH, M is a hydrogen atom. The above sulfonate residue may, for example, be a C$_{1-6}$ alkyl such as methyl or ethyl; or phenyl which may be substituted by C$_{1-6}$ alkyl.

In a case where T is halogen or —OSO$_2$G and M is sodium or potassium, the first step of the reaction (C) can be carried out usually in the presence of a solvent.

The solvent may be any solvent so long as it is inert to the reaction. For example, one or more types may suitably be selected for use from, for example, an ether such as diethyl ether, butyl ethyl ether, tetrahydrofuran, dioxane or dimethoxyethane; an aromatic hydrocarbon such as benzene, toluene or xylene; a dipolar aprotic solvent such as acetonitrile, propionitrile, N,N-dimethylformamide, dimethylsufoxide, hexamethylphosphoric triamide, sulfolane, dimethylacetamide or N-methylpyrrolidone; and an alcohol such as methanol, ethanol, propanol, n-butanol or tert-butanol.

In a case where T is halogen or —OSO$_2$G and M is sodium or potassium, the first step of the reaction (C) can be carried out usually from 0 to 150° C., preferably from 30 to 110° C. The reaction time is usually from about 0.5 to 24 hours, preferably from about 1 to 12 hours.

In a case where T is —OH and M is a hydrogen atom, the first step of the reaction (C) can be carried out usually by Mitsunobu Method. For example, it can be carried out by using a dialkyl azo dicarboxylate and triphenylphosphine in the presence of a solvent. Each of such a dialkyl azo dicarboxylate and triphenylphosphine may be used usually in an amount approximately equimolar to the compound of the formula (VI). The above dialkyl azo dicarboxylate may, for example, be diethyl azo dicarboxylate or diisopropyl azo dicarboxylate.

The solvent may be any solvent so long as it is inert to the reaction. For example, one or more types may suitably be selected for use from, for example, an ether such as diethyl ether, butyl ethyl ether, tetrahydrofuran, dioxane or dimethoxyethane; a halogenated hydrocarbon such as chlorobenzene, dichlorobenzene, dichloromethane, chloroform, carbon tetrachloride, dichloroethane, trichloroethane or dichloroethylene; and an aromatic hydrocarbon such as benzene, toluene or xylene.

In a case where T is —OH and M is a hydrogen atom, the first step of the reaction (C) can be carried out usually from 0 to 80° C., preferably from 20 to 60° C. The reaction time is usually from about 0.5 to 24 hours, preferably from about 1 to 16 hours.

The second step of the reaction (C) can be carried out usually by decomposing the compound of the formula (VIII) by means of hydrazine in the presence of a solvent. Such hydrazine may be used in an amount approximately equimolar to the compound of the formula (VIII).

The solvent may be any solvent so long as it is inert to the reaction. For example, one or more types may suitably be selected for use from, for example, an ether such as diethyl ether, butyl ethyl ether, tetrahydrofuran, dioxane or dimethoxyethane; an aromatic hydrocarbon such as benzene, toluene or xylene; and an alcohol such as methanol, ethanol, propanol, n-butanol or tert-butanol.

The second step of the reaction (C) can be carried out usually from 0 to 140° C., preferably from 30 to 100° C. The reaction time is usually from about 0.5 to 24 hours, preferably from about 2 to 12 hours.

Preferred embodiments of pesticides containing the compounds of the present invention will be described below. The pesticides containing the compounds of the present invention are particularly useful, for example, as agents for controlling various pests which become problematic in the agricultural and horticultural fields, i.e. agricultural and horticultural pesticides, or as agents for controlling pests which are parasitic on animals i.e. pesticides against parasites on animals. The agricultural and horticultural pesticides containing the compounds of the present invention are useful as an insecticide, a miticide, a nematicide and a soil-pesticide, and they are effective for controlling plant parasitic mites such as two-spotted spider mite (*Tetranychus urticae*), carmine spider mite (*Tetranychus cinnabarinus*), kanzawa spider mite (*Tetranychus kanzawai*) citrus red mite (*Panonychus citri*), European red mite (*Panonychus ulmi*), broad mite (*Polyphagotarsonemus latus*) pink citrus rust mite (*Aculops pelekassi*) and bulb mite (*Rhizoglyphus echinopus*); agricultural insect pests such as diamondback moth (*Plutella xylostella*), cabbage armyworm (*Mamestra brassicae*), common cutworm (*Spodoptera litura*), codling moth (*Laspeyresia pomonella*), bollworm (*Heliothis zea*), tobacco budworm (*Heliothis virescens*) gypsy moth (*Lymantria dispar*), rice leafroller (*Cnaphalocrocis medinalis*), *Adoxophyes* sp., summer fruit tortrix (*Adoxophyes orana fasciata*), peach fruit moth (*Carposina niponensis*), oriental fruit moth (*Grapholita molesta*), black cutworm (*Agrotis ipsilon*), cutworm (*Agrotis segetum*), colorado potato beetle (*Leptinotarsa decemlineata*), cucurbit leaf beetle (*Aulacophora femoralis*), boll weevil (*Anthonomus grandis*), aphids, planthoppers, leafhoppers, scales, bugs, whiteflies, thrips, grasshoppers, anthomyiid flies, scarabs, ants, leafminer flies; plant parasitic nematodes such as root-knot nematodes, cyst nematodes, root-lesion nematodes, rice white-tip nematode (*Aphelenchoides besseyi*), strawberry bud nematode (*Nothotylenchus acris*), pine wood nematode (*Bursaphelenchus lignicolus*); gastropods such as slugs and snails; soil pests such as isopods such as pillbugs (*Armadilidium vulgare*) and pillbugs (*Porcellio scaber*); hygienic insect pests such as tropical rat mite (*Ornithonyssus bacoti*), housefly (*Musca domestics*), house mosquito (*Culex pipiens*) and cockroachs; stored grain insect pests such as angoumois grai moth (*Sitotroga cerealella*), adzuki bean weevil (*Callosobruchus chinensis*), red flour beetle (*Tribolium castaneum*) and mealworms; clothes, house and household insect pests such as casemaking clothes moth (*Tinea pellionella*), black carpet beetle (*Anthrenus scrophularidae*) and subterranean termites; domestic mites such as mold mite (*Tyrophagus putrescentiae*), *Dermatophagoides farinae* and *Chelacaropsis moorei*. Among them, the agricultural and horticultural pesticides containing the compounds of the present invention are particularly effective for controlling plant parasitic mites, agricultural insect pests, plant parasitic nematodes or the like. Further, they are effective against insect pests having acquired resistance to organophosphorus, carbamate and/or synthetic pyrethroid insecticides. Moreover, the compounds of the present invention have excellent systemic properties, and by the application of the compounds of the present invention to soil treatment, not only noxious insects, noxious mites, noxious nematodes, noxious gastropods and noxious isopods in soil but also foliage pests can be controlled.

Another preferred embodiments of the pesticides containing compounds of the present invention may be agricultural and horticultural pesticides which collectively control the above-mentioned plant parasitic mites, agricultural insect pests, plant parasitic nematodes, gastropods and soil pests.

The agricultural and horticultural pesticide containing the compound of the present invention, is usually formulated by mixing the compound with various agricultural adjuvants and used in the form of a formulation such as a dust, granules, water-dispersible granules, a wettable powder, a water-based suspension concentrate, an oil-based suspension concentrate, water soluble granules, an emulsifiable concentrate, a soluble concentrate, a paste, an aerosol or an ultra low-volume formulation. However, so long as it is suitable for the purpose of the present invention, it may be formulated into any type of formulation which is commonly used in this field. Such agricultural adjuvants include solid carriers such as diatomaceous earth, slaked lime, calcium carbonate, talc, white carbon, kaoline, bentonite, a mixture of kaolinite and sericite, clay, sodium carbonate, sodium bicarbonate, mirabilite, zeolite and starch; solvents such as water, toluene, xylene, solvent naphtha, dioxane, acetone, isophorone, methyl isobutyl ketone, chlorobenzene, cyclohexane, dimethylsulfoxide, N,N-dimethylformamide, dimethylacetamide, N-methyl-2-pyrrolidone, and alcohol; anionic surfactants and spreaders such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, and a salt of a condensate of naphthalene sulfonate with formalin; nonionic surfactants and spreaders such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyethylene glycol, a polyoxyethylene fatty acid ester, a polyoxyethylene sorbitan fatty acid ester, a polyoxyethylene glycerin fatty acid ester, a polyoxyethylene hydrogenated castor oil, and a polyoxypropylene fatty acid ester; and vegetable and mineral oils such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil, and liquid paraffins. Each of the components as such adjuvants may be one or more suitably selected for use, so long as the purpose of the present invention can thereby be accomplished. Further, various additives which are commonly used, such as a filler, a thickener, an anti-settling agent, an anti-freezing agent, a dispersion stabilizer, a phytotoxicity reducing agent, and an anti-mold agent, may also be employed.

The weight ratio of the compound of the present invention to the various agricultural adjuvants is usually from 0.001:99.999 to 95:5, preferably from 0.005:99.995 to 90:10.

In the actual application of such a formulation, it may be used as it is, or may be diluted to a predetermined concentration with a diluent such as water, and various spreaders e.g. surfactants, vegetable oils or mineral oils may be added thereto, as the case requires.

The application of the agricultural and horticultural pesticide containing the compound of the present invention can not generally be defined, as it varies depending upon the weather conditions, the type of the formulation, the application season, the application site or the types or degree of outbreak of the pest insects. However, it is usually applied in a concentration of the active ingredient being from 0.05 to 800,000 ppm, preferably from 0.5 to 500,000 ppm, and the dose per unit area is such that the compound of the present invention is from 0.05 to 50,000 g, preferably from 1 to 30,000 g, per hectare. Further, agricultural and horticultural pesticides as another preferred embodiment of pesticides containing the compounds of the present invention may be applied in accordance with the above-described application of pesticides. The present invention includes such a method for controlling pests, particularly for controlling plant parasitic mites, agricultural insect pests or plant parasitic nematodes by such applications.

Various formulations of agricultural and horticultural pesticides containing the compounds of the present invention or their diluted compositions may be applied by conventional methods for application which are commonly employed, such as spraying (e.g. spraying, jetting, misting, atomizing, powder or grain scattering or dispersing in water), soil application (e.g. mixing or drenching), surface application (e.g. coating, powdering or covering) or impregnation to obtain poisonous feed. Further, it is possible to feed domestic animals with a food containing the above active ingredient and to control the outbreak or growth of pests, particularly insect pests, with their excrements. Furthermore, the active ingredient may also be applied by a so-called ultra low-volume application method. In this method, the composition may be composed of 100% of the active ingredient.

Further, the agricultural and horticultural pesticides containing compounds of the present invention may be mixed with or may be used in combination with other agricultural chemicals, fertilizers or phytotoxicity-reducing agents, whereby synergistic effects or activities may sometimes be obtained. Such other agricultural chemicals include, for example, a herbicide, an insecticide, a miticide, a nematicide, a soil pesticide, a fungicide, an antivirus agent, an attractant, an antibiotic, a plant hormone and a plant growth regulating agent. Especially, with a mixed pesticide having a compound of the present invention mixed with or used in combination with one or more active compounds of other agricultural chemicals, the application range, the application time, the pesticidal activities, etc. may be improved to preferred directions. The compound of the present invention and the active compounds of other agricultural chemicals may separately be formulated so that they may be mixed for use at the time of application, or they may be formulated together. The present invention includes such a mixed pesticidal composition.

The mixing ratio of the compound of the present invention to the active compounds of other agricultural chemicals can not generally be defined, since it varies depending upon the weather conditions, the types of formulations, the application time, the application site, the types or degree of outbreak of insect pests, etc., but it is usually within a range of from 1:300 to 300:1, preferably from 1:100 to 100:1, by weight. Further, the dose for the application is such that the total amount of the active compounds is from 0.1 to 50,000 g, preferably from 1 to 30,000 g, per hectare. The present invention includes a method for controlling pests by an application of such a mixed pesticide composition.

The active compounds of insect pest control agents such as insecticides, miticides, nematicides or soil pesticides in the above-mentioned other agricultural chemicals, include, for example, (by common names, some of them are still in an application stage) organic phosphate compounds such as Profenofos, Dichlorvos, Fenamiphos, Fenitrothion, EPN, Diazinon, Chlorpyrifos-methyl, Acephate, Prothiofos, Fosthiazate, Phosphocarb, Cadusafos, Disulfoton, Chlorpyrifos, Demeton-S-methyl, Dimethoate, Methamidophos and Parathion; carbamate compounds such as Carbaryl, Propoxur, Aldicarb, Carbofuran, Thiodicarb, Methomyl, Oxamyl, Ethiofencarb, Pirimicarb, Fenobucarb, Carbosulfan, and Benfuracarb; nereistoxin derivatives such as Cartap, and Thiocyclam, and Bensultap; organic chlorine compounds such as Dicofol, Tetradifon and Endosulfan; organometallic compounds such as Fenbutatin Oxide; pyrethroid compounds such as Fenvalerate, Permethrin, Cypermethrin, Deltamethrin, Cyhalothrin, Tefluthrin, Ethofenprox, Fenpropathrin and Bifenthrin; benzoylurea compounds such as Diflubenzuron, Chlorfluazuron, Teflubenzuron, Flufenoxuron, Lufenuron, Novaluron, Bistrifluoron and Noviflumuron; juvenile hormone-like compounds such as Methoprene, Pyriproxyfen, and Fenoxycarb; pyridazinone compounds such as Pyridaben; pyrazole compounds such as Fenpyroximate, Fipronil, Tebufenpyrad, Ethiprole, Tolfenpyrad, Acetoprole, Pyrafluprole and Pyriprole; neonicotinoids such as Imidacloprid, Nitenpyram, Acetamiprid, Thiacloprid, Thiamethoxam, Clothianidin, and Dinotefuran; hydrazine compounds such as Tebufenozide, Methoxyfenozide, Chromafenozide and Halofenozide; dinitro compounds; organic sulfur compounds; urea compounds; triazine compounds; hydrazone compounds; and other compounds, such as Flonicamid, Buprofezin, Hexythiazox, Amitraz, Chlordimeform, Silafluofen, Triazamate, Pymetrozine, Pyrimidifen, Chlorfenapyr, Indoxacarb, Acequinocyl, Etoxazole, Cyromazine, 1,3-dichloropropene, Diafenthiuron, Benclothiaz, Flufenerim, Pyridalyl, Spirodiclofen, Bifenazate, Spiromesifen, Propargite, Clofentezine, Fluacrypyrim, Flubendiamide, Cyflumetofen, Metaflumizone and Amidoflumet. Further, microbial agricultural chemicals such as BT agents, insect viruses, entomopathogenic fungi, and nematophagous fungi, antibiotics such as Avermectin, Emamectin-Benzoate, Milbemectin, Spinosad, Ivermectin and Lepimectin or natural products such as Azadirachtin, and Rotenone, may be used in admixture or in combination. The active compounds of fungicides among the above-mentioned other agricultural chemicals include, for example, (by common names, some of which are still in an application stage) pyrimidinamine compounds such as Mepanipyrim, Pyrimethanil, and Cyprodinil; azole compounds such as Triadimefon, Bitertanol, Triflumizole, Etaconazole, Propiconazole, Penconazole, Flusilazole, Myclobutanil, Cyproconazole, Terbuconazole, Hexaconazole, Furconazole-cis, Prochloraz, Metconazole, Epoxiconazole, Tetraconazole, Oxpoconazole, and Sipconazole; quinoxaline compounds such as Quinomethionate; dithiocarbamate compounds such as Maneb, Zineb, Mancozeb, Polycarbamate, Propineb; organic chlorine compounds such as Fthalide, Chlorothalonil, and Quintozene; imidazole compounds such as Benomyl, Thiophanate-Methyl, Carbendazim, and Cyazofamid; pyridinamine compounds such as Fluazinam; cyanoacetamide compounds such as Cymoxanil; phenylamide compounds such as Metalaxyl, Oxadixyl, Ofurace, Benalaxyl, Furalaxyl, and Cyprofuram; sulfenic acid compounds such as Dichlofluanid; copper compounds such as cupric hydroxide, and Oxine Copper; isoxazole compounds such as Hydroxyisoxazole; organophosphorus compounds such as Fosetyl-Al, Tolclofos-Methyl, S-benzyl O,O-diisopropylphosphorothioate, O-ethyl S,S-diphenylphosphorodithioate, and aluminumethylhydrogen phosphonate; N-halogenothioalkyl compounds such as Captan, Captafol, and Folpet; dicarboximide compounds such as Procymidone, Iprodione, and Vinclozolin; benzanilide compounds such as Flutolanil, Mepronil, and Zoxamide; piperazine compounds such as Triforine; pyridine compounds such as Pyrifenox; carbinol compounds such as Fenarimol; and Flutriafol; piperidine compounds such as Fenpropidine; morpholine compounds such as Fenpropimorph; organotin compounds such as Fentin Hydroxide, and Fentin Acetate; urea compounds such as Pencycuron; cinnamic acid compounds such as Dimethomorph; phenylcarbamate compounds such as Diethofencarb; cyanopyrrole compounds such as Fludioxonil, and Fenpiclonil; Strobilurin compounds such as Azoxystrobin, Kresoxim-Methyl, Metominofen, Trifloxystrobin, Picoxystrobin, and Pyraclostrobin; oxazolidinedione compounds such as Famoxadone; thiazole carboxamide compounds such as Ethaboxam; silyl amide compounds such as Silthiopham; aminoacid amidecarbamate compounds such as Iprovalicarb; imidazolidine compound such as Fenamidone; hydroxyanilide compounds such as Fenhexamid; benzene sulfonamide compounds such as Flusulfamide; anthraquinone compounds; crotonic acid compounds; antibiotics; and other compounds, such as Isoprothiolane, Tricyclazole, Pyroquilon, Diclomezine, Probenazole, Quinoxyfen, Propamocarb Hydrochloride, Spiroxamine, Chloropicrin, Dazomet, and Metam-Sodium.

Further, agricultural chemicals which may be used in admixture with or in combination with the compounds of the present invention, may, for example, be the active ingredient compounds in the herbicides as disclosed in Farm Chemicals Handbook (2002 edition), particularly those of soil treatment type.

The pesticides against parasites on animals are effective for controlling e.g. external parasites which are parasitic on the body surface of host animals (such as the back, the axilla, the lower abdomen or inside of the thigh) or internal parasites which are parasitic in the body of host animals (such as the stomach, the intestinal tract, the lung, the heart, the liver, the blood vessels, the subcutis or lymphatic tissues), but they are particularly effective for controlling the external parasites.

The external parasites may, for example, be animal parasitic acarina or fleas. Their species are so many that it is difficult to list all of them, and therefore, their typical examples will be given.

The animal parasitic acarina may, for example, be ticks such as *Boophilus microplus, Rhipicephalus sanguineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor reticulatus*, and *Dermacentor taiwanesis*; common red mite (*Dermanyssus gallinae*); northern fowl mites such as *Ornithonyssus sylviarum*, and *Ornithonyssus bursa*; trombidioids such as *Eutrombicula wichmanni, Leptotrombidium akamushi, Leptotrombidium pallidum, Leptotrombidium fuji, Leptotrombidium tosa, Neotrombicula autumnalis, Eutrombicula alfreddugesi*, and *Helenicula miyagawai*; cheyletidae such as *Cheyletiella yasguri, Cheyletiella parasitivorax*, and *Cheyletiella blakei*; sarcoptic mange mites such as *Psoroptes cuniculi, Chorioptes bovis, Otodectes cynotis, Sarcoptes scabiei*, and *Notoedres cati*; and Demodicidae such as *Demodex canis*. The pesticides against parasites on animals, containing the compounds of the present invention, are particularly effective for the control of ticks among them.

The fleas may, for example, be externally parasitic wingless insects belonging to *Siphonaptera*, more specifically, fleas belonging to *Pulicidae, Ceratephyllus*, etc. Fleas belonging to Pulicidae may for example, be *Ctenocephalides canis, Ctenocephalides felis, Pulex irritans, Echidnophaga gallinacea, Xenopsylla cheopis, Leptopsylla segnis, Nosopsyllus fasciatus*, and *Monopsyllus anisus*. The pesticides against parasites on animals, containing the compounds of the present invention, are particularly effective for the control of fleas belonging to Pulicidae, particularly *Ctenocephalides canis* and *Ctenocephalides felis*, among them.

Other external parasites may, for example, be sucking lice (Anoplura) such as shortnosed cattle louse (*Haematopinus*

*eurysternus*), horse sucking louse (*Haematopinus asini*), sheep louse, longnosed cattle louse (*Linognathus vituli*), and head louse (*Pediculus capitis*); biting lice such as dog biting louse (*Trichodectes canis*); and blood-sucking dipterous insects such as horsefly (*Tabanus trigonus*), biting midges (*Culicoides schultzei*), and blackfly (*Simulium ornatum*). Further, the internal parasites may, for example, be nematodes such as lung worms, whipworms (*Trichuris*), tuberous worms, gastric parasites, ascaris, and filarioidea; cestoda such as *Spirometra erinacei, Diphyllobothrium latum, Dipylidium caninum, Taenia multiceps, Echinococcus granulosus, Echinococcus multilocularis*, trematoda such as *Schistosoma japonicum, Fasciola hepatica*; and protozoa such as coccidia, malaria parasites (*Plasmodium malariae*), intestinal sarcocyst, toxoplasma, and cryptosporidium.

The host animals may, for example, be pet animals, domestic animals, and poultry, such as dogs, cats, mice, rats, hamsters, guinea pigs, squirrels, rabbits, ferrets, birds (such as pigeons, parrots, hill mynas, Java sparrows, honey parrots, lovebirds and canaries), cows, horses, pigs, sheep, ducks and chickens. The pesticides against parasites on animals, containing the compounds of the present invention, are particularly effective for the control of pests parasitic on pet animals or domestic animals, especially for the control of external parasites, among them. Among pet animals or domestic animals, they are effective particularly for dogs, cats, cows and horses.

When the compound of the present invention is used as a pesticide against parasites on animals, it may be used as it is or may be used together with suitable adjuvants, as formulated into various formulations such as a dust, granules, tablets, a powder, capsules, a soluble concentrate, an emulsifiable concentrate, a water-based suspension concentrate and an oil-based suspension concentrate. In addition to such formulations, it may be formulated into any type of formulation which is commonly used in this field, so long as it is suitable for the purpose of the present invention. The adjuvants to be used for formulations may, for example, be anionic surfactants or nonionic surfactants exemplified above as adjuvants for formulation of agricultural and horticultural pesticides; a cationic surfactant such as cetyl trimethylammonium bromide; a solvent such as water, acetone, acetonitrile, monomethylacetamide, dimethylacetamide, dimethylformamide, 2-pyrrolidone, N-methyl-2-pyrrolidone, kerosene, triacetin, methanol, ethanol, isopropanol, benzyl alcohol, ethylene glycol, propylene glycol, polyethylene glycol, liquid polyoxyethylene glycol, butyl diglycol, ethylene glycol monomethyl ether, ethylene glycol monoethyl ether, diethylene glycol monoethyl ether, diethylene glycol n-butyl ether, dipropylene glycol monomethyl ether, or dipropylene glycol n-butyl ether; an antioxidant such as butylhydroxyanisole, butylhydroxytoluene, ascorbic acid, sodium hydrogenmetasulfite, propyl gallate or sodium thiosulfate; a coating film-forming agent such as polyvinylpyrrolidone, polyvinyl alcohol, or a copolymer of vinyl acetate and vinyl pyrrolidone; the vegetable oils and mineral oils as exemplified above as adjuvants for formulation of agricultural and horticultural pesticides; and a carrier such as lactose, sucrose, glucose, starch, wheat flour, corn powder, soybean cake and meal, defatted rice bran, calcium carbonate or other commercially available feed materials. One or more of the respective components of these adjuvants may be suitably selected for use, so long as such will not depart from the purpose of the present invention. Further, other than the above-mentioned adjuvants, some among those known in this field may suitably be selected for use, and still further, some among the above-mentioned various adjuvants to be used in the agricultural and horticultural field may suitably be selected for use.

The blend ratio of the compound of the present invention to various adjuvants is usually from 0.1:99.9 to 90:10. In the actual use of such a formulation, it may be used as it is, or may be diluted to a predetermined concentration with a diluent such as water, and various spreaders (e.g. surfactants, vegetable oils or mineral oils) may be added thereto, as the case requires.

Administration of the compound of the present invention to a host animal is carried out orally or parenterally. As an oral administration method, a method of administering a tablet, a liquid agent, a capsule, a wafer, a biscuit, a minced meat or other feed, containing the compound of the present invention, may be mentioned. As a parenteral administration method, there may, for is example, be mentioned a method wherein the compound of the present invention is formulated into a suitable formulation and then taken into the body by e.g. intravenous administration, intramuscular administration, intradermal administration, hypodermic administration, etc.; a method wherein it is administered on the body surface by spot-on treatment, pour-on treatment or spray treatment; or a method of embedding a resin fragment or the like containing the compound of the present invention under the skin of the host animal.

The dose of the compound of the present invention to a host animal varies depending upon the administration method, the purpose of administration, the diseased symptom, etc., but it is usually administered in a proportion of from 0.01 mg to 100 g, preferably from 0.1 mg to 10 g, per 1 kg of the body weight of the host animal.

The present invention also includes a method for controlling a pest by the above-mentioned administration method or by the above-mentioned dose, particularly a method for controlling external parasites or internal parasites.

Further, in the present invention, there may be a case where by controlling pests parasitic on animals as described above, it is possible to prevent or cure various diseases of the host animal thereby caused. Thus, the present invention also includes a preventive or therapeutic agent for an animal disease caused by parasite, containing the compound of the present invention as an active ingredient, and a method for preventing or curing an animal disease caused by parasite.

When the compound of the present invention is used as a pesticide against parasites on animals, various vitamins, minerals, amino acids, nutrients, enzymes, antipyretics, sedatives, antiphlogistics, fungicides, colorants, aromatic substances, preservatives, etc., may be used in admixture with or in combination with the adjuvants. Further, as the case requires, other animal drugs or agricultural chemicals, such as vermicides, anti-coccidium agents, insecticides, miticides, pulicides, nematocides, bactericides or antibacterial agents, may be mixed or combined for use, whereby improved effects may sometimes be obtained. The present invention includes such a mixed pesticidal composition having the above-mentioned various components mixed or combined for use, and further a method for controlling a pest by using it, particularly a method for controlling external parasites or internal parasites.

Now, some of preferred embodiments of the compounds of the present invention will be exemplified. Among the exemplified, with respect to the following (1) to (8), optional two or more may suitably be combined, and compounds based on such combinations are also preferred embodiments of the compounds of the present invention. Further, pesticides, agricultural and horticultural pesticides, insecticides, miticides, nematicides, pesticides against parasites on animals, pesticides against external parasites on animals and preventive or therapeutic agents for animal diseases caused by parasites, containing the following compounds as active ingredients, are also preferred embodiments in the present invention. Further, methods for controlling pests thereby applying effective amounts of the following compounds, are also preferred embodiments in the present invention. However, it should be understood that the present invention is by no means thereby restricted.

(1) A compound of the above formula (I) wherein at least one of $R^1$ is substituted at the 4-position, and such $R^1$ is a fluorine atom or a chlorine atom.

(2) A compound of the above formula (I) wherein at least one of $R^1$ is substituted at the 4-position, and such $R^1$ is a chlorine atom.

(3) A compound of the above formula (I) wherein at least one of $R^1$ is substituted at the 4-position, and such $R^1$ is alkyl, haloalkyl, alkenyl, haloalkenyl, alkynyl, haloalkynyl, alkoxy, haloalkoxy, alkylcarbonyl, haloalkylcarbonyl, alkoxycarbonyl, haloalkoxycarbonyl, phenoxy carbonyl which may be substituted, nitro or formyl.

(4) A compound of the above formula (I) wherein $R^2$ is halogen, haloalkyl or haloalkoxy.

(5) A compound of the above formula (I) wherein $R^3$ is halogen.

(6) A compound of the above formula (I) wherein $R^3$ is halogen and 3-or 5-monosubstituted, or 3,5-disubstituted.

(7) A compound of the above formula (I) wherein Y is cyclopropyl.

(8) A compound of the above formula (I) wherein Y is cyclopropyl, and such cyclopropyl is substituted by 1 to 5 substituents selected from the group consisting of halogen, alkyl and haloalkyl.

(9) A compound of the above formula (I) wherein $R^1$ is halogen, alkyl, haloalkyl, alkylcarbonyl or formyl; $R^2$ is halogen, haloalkyl or haloalkoxy; $R^3$ is halogen or haloalkyl; A is alkyl substituted by Y; Y is cyclopropyl which may be substituted by at least one substituent selected from the group consisting of halogen and alkyl; m is 1 or 2; n is 0; and q is 1.

(10) A compound as defined in the above (9), wherein $R^1$ is 2-monosubstituted or 2,4-disubstituted, and $R^3$ is 3-monosubstituted.

(11) A compound of the above formula (I) wherein $R^1$ is halogen, alkyl or haloalkyl, $R^2$ is halogen, haloalkyl or haloalkoxy, $R^3$ is halogen, A is alkyl substituted by Y, Y is cyclopropyl, m is 2, n is 0, and q is 1.

(12) A compound as defined in the above (11) wherein $R^1$ is 2,4-disubstituted, and $R^3$ is 3-monosubstituted.

(13) A compound as defined in the above (12) wherein $R^1$ at the 4-position is a chlorine atom.

(14) A compound of the formula (I) which is represented by the formula (I-1):

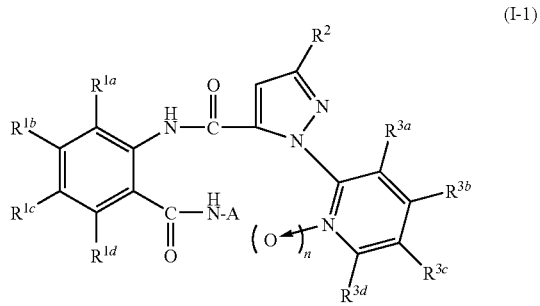

wherein $R^{1a}$ is halogen or alkyl; each of $R^{1b}$ and $R^{1d}$ is a hydrogen atom; $R^{1c}$ is alkyl, haloalkyl, alkenyl, haloalkenyl, alkynyl, haloalkynyl, alkoxy, haloalkoxy, alkylcarbonyl, haloalkylcarbonyl, alkoxycarbonyl, haloalkoxycarbonyl, phenoxycarbonyl which may be substituted, nitro or formyl; $R^2$ is halogen, haloalkyl or haloalkoxy; $R^{3a}$ is halogen or haloalkyl; each of $R^{3b}$, $R^3$ and $R^{3d}$ is a hydrogen atom; A is alkyl substituted by Y; Y is cyclopropyl which may be substituted by 1 to 5 substituents selected from the group consisting of halogen, alkyl and haloalkyl; and n is 0

(15) A compound as defined in the above (14) wherein $R^{1c}$ is haloalkyl, alkylcarbonyl or formyl.

(16) A compound as defined in the above (14) wherein $R^{1c}$ is haloalkyl.

(17) A compound as defined in the above (14) wherein Y is cyclopropyl.

(18) A compound of the formula (I) which is represented by the formula (Ia):

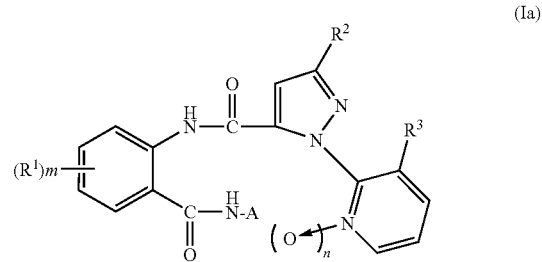

wherein $R^1$ is halogen or alkyl; each of $R^2$ and $R^3$ is halogen or $-CF_3$; A is alkyl substituted by Y; Y is $C_{3-4}$ cycloalkyl which may be substituted by halogen or alkyl; m is 1 or 2; and n is 0 or 1.

(19) A compound of the formula (I) which is represented by the above formula (Ia) wherein $R^1$ is halogen or alkyl; each of $R^2$ and $R^3$ which are independent of each other is halogen or $-CF_3$; A is $-X-Y$; X is alkylene; Y is $C_{3-4}$ cycloalkyl which may be substituted by halogen or alkyl; m is 1 or 2; and n is 0 or 1.

EXAMPLES

Now, the present invention will be described with reference to Examples, but it should be understood that the present invention is by no means limited thereto. Firstly, Preparation Examples of the compound of the present invention will be described.

Preparation Example 1

Preparation of N-[6-[[(cyclopropylmethyl)amino] carbonyl]-2-methylphenyl]-1-(3-chloro-2-pyridyl)-3-(trifluoromethyl)-1H-pyrazol-5-carboxamide (aftermentioned compound No. 1)

1.49 g of triethylamine was gradually dropwise added to a mixed solution comprising 0.8 g of cyclopropylmethylamine hydrochloride and 40 ml of tetrahydrofuran under cooling with ice, followed by stirring at room temperature for 30 minutes. Then, a mixed solution comprising 1 g of 2-[1-(3-chloro-2-pyridyl)-3-(trifluoromethyl)-1H-pyrazol-5-yl]-8-methyl-4H-3,1-benzoxazin-4-one and 10 ml of tetrahydrofuran was gradually dropwise added. After completion of the dropwise addition, the mixed solution was reacted for 4 hours under reflux. After completion of the reaction, the solvent was distilled off under reduced pressure, and to the residue, ethyl acetate and water were added for extraction. The organic layer was washed with water and a saturated sodium chloride aqueous solution and dried over anhydrous magnesium sulfate. The solvent was distilled off under reduced pressure, and the residue was purified by silica gel column chromatography (eluent: n-hexane/ethyl acetate=1/1) to obtain 0.54 g of the desired product having a melting point of 199.4° C.

Prepapation Example 2

Preparation of N-[4-chloro-2-methyl-6-[[1-methyl-(cyclopropylmethyl)amino]carbonyl]-phenyl]-3-(trifluoromethyl)-1-(3-chloro-2-pyridyl)-1H-pyrazol-5-carboxamide (after-mentioned compound No. 3)

1.37 g of triethylamine was gradually dropwise added to a mixed solution comprising 0.82 g of α-methyl-cyclopropyl-methylamine hydrochloride and 40 ml of tetrahydrofuran under cooling with ice, followed by stirring at room temperature for 30 minutes. Then, a mixed solution comprising 1 g of 2-[1-(3-chloro-2-pyridyl)-3-(trifluoromethyl)-1H-pyrazol-5-yl]-6-chloro-8-methyl-4H-3,1-benzoxazin-4-one and 10 ml of tetrahydrofuran were gradually dropwise added. After completion of the dropwise addition, the mixed solution was reacted for 4 hours under reflux. After completion of the reaction, the solvent was distilled off under reduced pressure, and to the residue, ethyl acetate and water were added for extraction. The organic layer was washed with water and a saturated sodium chloride aqueous solution and dried over anhydrous magnesium sulfate. The solvent was distilled off under reduced pressure, and the residue was purified by silica gel column chromatography (eluent: n-hexane/ethyl acetate=1/1) to obtain 0.45 g of the desired product having a melting point of 210.0° C.

Preparation Example 3

Preparation of N-[4-chloro-2-methyl-6-[[α-methyl-(cyclopropylmethyl)amino]carbonyl]-phenyl]-3-bromo-1-(3-chloro-2-pyridyl)-1H-pyrazol-5-carboxamide (after-mentioned compound No. 9)

1.07 g of triethylamine was gradually dropwise added to a mixed solution comprising 0.65 g of α-methyl-cyclopropyl-methylamine hydrochloride and 40 ml of tetrahydrofuran under cooling with ice, followed by stirring at room temperature for 30 minutes. Then, a mixed solution comprising 0.8 g of 2-[3-bromo-1-(3-chloro-2-pyridyl)-1H-pyrazol-5-yl]-6-chloro-8-methyl-4H-3,1-benzoxazin-4-one and 10 ml of tetrahydrofuran was gradually dropwise added. After completion of the dropwise addition, the mixed solution was reacted for 4 hours under reflux. After completion of the reaction, the solvent was distilled off under reduced pressure, and to the residue, ethyl acetate and water were added for extraction. The organic layer was washed with water and a saturated sodium chloride aqueous solution and dried over anhydrous magnesium sulfate. The solvent was distilled off under reduced pressure, and the residue was purified by silica gel column chromatography (eluent: n-hexane/ethyl acetate=1/1) to obtain 0.33 g of the desired product having a melting point of 183.6° C.

Preparation Example 4

Preparation of N-[2-bromo-4-chloro-6-[[α-methyl-(cyclopropylmethyl)amino]carbonyl]-phenyl]-3-bromo-1-(3-chloro-2-pyridyl)-1H-pyrazol-5-carboxamide (after-mentioned compound No. 16)

1 g of triethylamine was gradually dropwise added to a mixed solution comprising 0.6 g of α-methyl-cyclopropylm-ethylamine hydrochloride and 40 ml of tetrahydrofuran under cooling with ice, followed by stirring for 1 hour at room temperature. Then, a mixed solution comprising 0.85 g of 2-[3-bromo-1-(3-chloro-2-pyridyl)-1H-pyrazol-5-yl]-6-chloro-8-bromo-4H-3,1-benzoxazin-4-one and 10 ml of tetrahydrofuran was gradually dropwise added. After completion of the dropwise addition, the mixed solution was reacted for 4 hours under reflux. After completion of the reaction, the solvent was distilled off, and to the residue, ethyl acetate and water were added for extraction. The organic layer was washed with water and a saturated sodium chloride aqueous solution and dried over anhydrous magnesium sulfate. The solvent was distilled off under reduced pressure, and the residue was purified by silica gel column chromatography (eluent: n-hexane/ethyl acetate=1/2) to obtain 0.7 g of the desired product having a melting point of 260.6° C.

Now, typical examples of the compound of the present invention represented by the above formula (I) will be given in Table 1. These compounds can be prepared by the above-described Preparation Examples or by the above-mentioned various processes for the production of the compound of the present invention.

In Table 1, No. represents compound No. Further, in Table 1, Me represents a methyl group, Et an ethyl group, iPr an isopropyl group, CPr a cyclopropyl group, CBu a cyclobutyl group, and Ph a phenyl group. Further, in Table 1, A1 represents —CH$_2$—[CPr], A2-CH(Me)-[CPr], A3-CH$_2$—[2-Me-CPr], A4-CH$_2$— [2,2-Cl$_2$-1-Me-CPr], A5-CH$_2$— [1-Me-CPr], and A6-CH (Me)-[CBu]. Further, in Table 1, 2-Me-CPr represents a cyclopropyl group having a methyl group substituted at the 2-position, and CO$_2$Ph(4-Cl) represents a phenoxycarbonyl group having a chlorine atom substituted at the 4-position of the phenyl group. The same applies to other similar descriptions.

Further, in Table 1, n is 0 unless otherwise specified.

TABLE 1

(I-1)

| No. | $R^{1a}$ | $R^{1b}$ | $R^{1c}$ | $R^{1d}$ | $R^2$ | $R^{3a}$ | $R^{3b}$ | $R^{3c}$ | $R^{3d}$ | A | Physical properties (mp: °C.) |
|---|---|---|---|---|---|---|---|---|---|---|---|
| 1 | Me | H | H | H | $CF_3$ | Cl | H | H | H | A1 | 199.4 |
| 2 | Me | H | Cl | H | $CF_3$ | Cl | H | H | H | A1 | 216.4 |
| 3 | Me | H | Cl | H | $CF_3$ | Cl | H | H | H | A2 | 210.0 |
| 4 | Me | H | Cl | H | $CF_3$ | Cl | H | H | H | A3 | |
| 5 | Me | H | Cl | H | $CF_3$ | Cl | H | H | H | A4 | 219.3 |
| 6 | Me | H | Cl | H | Cl | Cl | H | H | H | A1 | |
| 7 | Me | H | Cl | H | Br | Cl | H | H | H | A1 | |
| 8 | Me | H | Cl | H | Cl | Cl | H | H | H | A2 | 186.7 |
| 9 | Me | H | Cl | H | Br | Cl | H | H | H | A2 | 183.6 |
| 10 | Me | H | Cl | H | $CF_3$ | Cl | H | H | H | A5 | 161.2 |
| 11 | Br | H | Cl | H | $CF_3$ | Cl | H | H | H | A2 | 158.2 |
| 12 | I | H | Br | H | $CF_3$ | Cl | H | H | H | A2 | 145.5 |
| 13 | Me | H | Cl | H | $CF_3$ | Cl | H | H | H | A2 | 230.9 |
| 14 | Cl | H | Cl | H | $CF_3$ | Cl | H | H | H | A2 | 238.8 |
| 15 | Cl | H | Cl | H | Br | Cl | H | H | H | A2 | 236.8 |
| 16 | Br | H | Cl | H | Br | Cl | H | H | H | A2 | 260.6 |
| 17 | I | H | Cl | H | Br | Cl | H | H | H | A2 | 251.4 |
| 18 | Br | H | F | H | $CF_3$ | Cl | H | H | H | A2 | 220.1 |
| 19 | I | H | Cl | H | $CF_3$ | Cl | H | H | H | A2 | 241.0 |
| 20 | Cl | H | F | H | $CF_3$ | Cl | H | H | H | A2 | 214.0 |
| 21 | I | H | I | H | $CF_3$ | Cl | H | H | H | A2 | 251.9 |
| 22 | Br | H | F | H | Br | Cl | H | H | H | A2 | 219.2 |
| 23 | Me | H | Cl | H | $CF_3$ | Br | H | H | H | A2 | 162-164 |
| 24 | Me | H | Cl | H | Cl | $CF_3$ | H | H | H | A2 | 154-156 |
| 25 | Me | H | Cl | H | Br | Br | H | H | H | A2 | 128-132 |
| 26 | Cl | H | F | H | Br | Cl | H | H | H | A2 | |
| 27 | I | H | F | H | Br | Cl | H | H | H | A2 | |
| 28 | F | H | Cl | H | Br | Cl | H | H | H | A2 | |
| 29 | F | H | Cl | H | $CF_3$ | Cl | H | H | H | A2 | |
| 30 | I | H | F | H | $CF_3$ | Cl | H | H | H | A2 | |
| 31 | F | H | F | H | $CF_3$ | Cl | H | H | H | A2 | |
| 32 | F | H | F | H | Br | Cl | H | H | H | A2 | |
| 33 | Me | H | F | H | $CF_3$ | Cl | H | H | H | A2 | |
| 34 | Me | H | F | H | Br | Cl | H | H | H | A2 | |
| 35 | Me | H | $CO_2Me$ | H | Br | Cl | H | H | H | A2 | |
| 36 | Me | H | $CO_2$-iPr | H | Br | Cl | H | H | H | A2 | |
| 37 | Me | H | $CO_2Ph$ | H | Br | Cl | H | H | H | A2 | |
| 38 | Br | H | Cl | H | Cl | Cl | H | H | H | A2 | 233.2 |
| 39 | Br | H | F | H | Cl | Cl | H | H | H | A2 | 179.1 |
| 40 | Me | H | $COCH_3$ | H | $CF_3$ | Cl | H | H | H | A2 | 143.4 |
| 41 | Me | H | CHO | H | $CF_3$ | Cl | H | H | H | A2 | 152.3 |
| 42 | Me | H | $CHF_2$ | H | $CF_3$ | Cl | H | H | H | A2 | 212.9 |
| 43 | Me | H | $CHF_2$ | H | Br | Cl | H | H | H | A2 | |
| 44 | Me | H | $CHF_2$ | H | Cl | Cl | H | H | H | A2 | |
| 45 | Et | H | Cl | H | $CF_3$ | Cl | H | H | H | A2 | 215.4 |
| 46 | Et | H | Cl | H | Br | Cl | H | H | H | A2 | |
| 47 | Et | H | Cl | H | Cl | Cl | H | H | H | A2 | |
| 48 | Me | H | $NO_2$ | H | $CF_3$ | Cl | H | H | H | A2 | 197.9 |
| 49 | Me | H | $NO_2$ | H | Br | Cl | H | H | H | A2 | |
| 50 | Me | H | $NO_2$ | H | Cl | Cl | H | H | H | A2 | |
| 51 | Me | H | $CF_3$ | H | Br | Cl | H | H | H | A2 | |
| 52 | Me | H | $CF_3$ | H | Cl | Cl | H | H | H | A2 | |
| 53 | Me | H | $CF_3$ | H | $CF_3$ | Cl | H | H | H | A2 | |
| 54 | $CF_3$ | H | Cl | H | Br | Cl | H | H | H | A2 | |
| 55 | Me | H | OMe | H | Br | Cl | H | H | H | A2 | |
| 56 | Me | H | OMe | H | $CF_3$ | Cl | H | H | H | A2 | |
| 57 | Me | H | OMe | H | Cl | Cl | H | H | H | A2 | |
| 58 | $OCHF_2$ | H | Cl | H | Cl | Cl | H | H | H | A2 | |
| 59 | $OCHF_2$ | H | Cl | H | Br | Cl | H | H | H | A2 | |
| 60 | $OCHF_2$ | H | Cl | H | $CF_3$ | Cl | H | H | H | A2 | |

TABLE 1-continued (I-1)

| No. | $R^{1a}$ | $R^{1b}$ | $R^{1c}$ | $R^{1d}$ | $R^2$ | $R^{3a}$ | $R^{3b}$ | $R^{3c}$ | $R^{3d}$ | A | Physical properties (mp: ° C.) |
|---|---|---|---|---|---|---|---|---|---|---|---|
| 61 | $CHF_2$ | H | Cl | H | $CF_3$ | Cl | H | H | H | A2 | |
| 62 | $CHF_2$ | H | Cl | H | Br | Cl | H | H | H | A2 | |
| 63 | $CHF_2$ | H | Cl | H | Cl | Cl | H | H | H | A2 | |
| 64 | Me | H | $CH=CH_2$ | H | $CF_3$ | Cl | H | H | H | A2 | |
| 65 | Me | H | $C\equiv CH$ | H | $CF_3$ | Cl | H | H | H | A2 | |
| 66 | Me | H | Cl | H | $CF_3$ | Cl | H | H | H | A6 | |
| 67 | Me | H | $COCF_3$ | H | Br | Cl | H | H | H | A2 | |
| 68 | Me | H | $CH=CCl_2$ | H | $CF_3$ | Cl | H | H | H | A2 | |
| 69 | Me | H | $C\equiv CI$ | H | $CF_3$ | Cl | H | H | H | A2 | |
| 70 | Me | H | $CO_2Ph(4-Cl)$ | H | Br | Cl | H | H | H | A2 | |
| 71 | Me | H | $CO_2Ph(4-Me)$ | H | $CF_3$ | Cl | H | H | H | A2 | |
| 72 | Me | H | $CO_2Ph(4-NO_2)$ | H | $CF_3$ | Cl | H | H | H | A2 | |
| 73 | Me | H | $CO_2Ph(4-CN)$ | H | $CF_3$ | Cl | H | H | H | A2 | |
| 74 | Me | H | $CO_2Ph(4-SMe)$ | H | $CF_3$ | Cl | H | H | H | A2 | |
| 75 | Et | H | Cl | H | $OCH_2CF_3$ | Cl | H | H | H | A2 | |
| 76 | Me | H | $NO_2$ | H | $OCH_2CF_3$ | Cl | H | H | H | A2 | |
| 77 | Me | H | $CHF_2$ | H | $CF_3$ | H | H | Cl | H | A2 | |
| 78 | Et | H | Cl | H | Br | H | H | F | H | A2 | |
| 79 | I | H | Cl | H | Br | F | H | F | H | A2 | |
| 80 | I | H | Cl | H | Cl | Cl | H | H | H | A2 | 220.6 |
| 81 | Me | H | Cl | H | $OCH_2CF_3$ | Cl | H | H | H | A2 | 175.1 |
| 82 | Br | H | $CHF_2$ | H | $CF_3$ | Cl | H | H | H | A2 | |
| 83 | Br | H | $CHF_2$ | H | Br | Cl | H | H | H | A2 | |
| 84 | Br | H | $CHF_2$ | H | Cl | Cl | H | H | H | A2 | |
| 85 | Me | H | Cl | H | $CF_3$ | Cl | H | Cl | H | A2 | |
| 86 | Me | H | Cl | H | $CF_3$ | Cl | H | F | H | A2 | |
| 87 | Br | H | $NO_2$ | H | Br | Cl | H | H | H | A2 | |
| 88 | Br | H | $NO_2$ | H | $CF_3$ | Cl | H | H | H | A2 | |
| 89 | Br | H | $NO_2$ | H | Cl | Cl | H | H | H | A2 | |
| 90 | I | H | Br | H | Cl | Cl | H | H | H | A2 | 222.9 |
| 91 | I | H | Br | H | Br | Cl | H | H | H | A2 | 221.0 |
| 92 | Me | H | Me | H | $CF_3$ | Cl | H | H | H | A2 | 172.3 |
| 93 | Me | H | $CO_2$-iPr | H | Br | Cl | H | H | H | A2 | 176-179 |
| 94 | Et | H | Br | H | $CF_3$ | Cl | H | H | H | A2 | 175.2 |
| 95 | Et | H | $NO_2$ | H | $CF_3$ | Cl | H | H | H | A2 | 116.8 |
| 96 | Me | H | $CO_2Me$ | H | Br | Cl | H | H | H | A2 | 190-198 |
| 97 | $CF_3$ | H | Cl | H | Br | Cl | H | H | H | A2 | |
| 98 | $CF_3$ | H | Br | H | $CF_3$ | Cl | H | H | H | A2 | 234.8 |
| 99 | $CF_3$ | H | Cl | H | $CF_3$ | Cl | H | H | H | A2 | 230.0 |
| 100 | Cl | H | $CF_3$ | H | Br | Cl | H | H | H | A2 | |
| 101 | Br | H | $CF_3$ | H | $CF_3$ | Cl | H | H | H | A2 | |
| 102 | Cl | H | $CF_3$ | H | $CF_3$ | Cl | H | H | H | A2 | |
| 103 | N-oxide of compound No. 1 (n = 1) | | | | | | | | | | |
| 104 | N-oxide of compound No. 3 (n = 1) | | | | | | | | | | |
| 105 | N-oxide of compound No. 9 (n = 1) | | | | | | | | | | |
| 106 | N-oxide of compound No. 16 (n = 1) | | | | | | | | | | |
| 107 | N-oxide of compound No. 22 (n = 1) | | | | | | | | | | |
| 108 | N-oxide of compound No. 42 (n = 1) | | | | | | | | | | |

Now, test examples will be described.

Test Example 1

Test on Controlling Effects Against Common Cutworm (*Spodoptera litura*)

A leaf segment of cabbage was dipped for about 10 seconds in an insecticidal solution prepared to bring the concentration of the compound of the present invention to 50 ppm or 3.1 ppm and dried in air. A wet filter paper was laid in a petri dish having a diameter of 9 cm, and the dried leaf segment of cabbage was placed thereon Ten second-third instar larvae common cutworm were released therein and after putting a cover, left in a constant temperature chamber at 25° C. with lightening. Dead larvae were counted 5 days after the release, and 3-5 the mortality was calculated by the following equation. Here, moribund insects were counted as dead insects.

The mortality at 50 ppm was obtained with respect to the above-mentioned compound Nos 8, 20 to 22, 25, 41, 91 to 93 and 96, whereby all compounds showed high controlling effects with a mortality of at least 90%, and the mortality at 3.1 ppm was obtained with respect to the above-mentioned compound Nos. 1 to 3, 5, 9 to 19, 23, 24, 38 to 40, 42, 80, 81 and 90, whereby all compounds showed high controlling effects with a mortality of at least 90%.

Mortality (%)=(number of dead insects/number of released insects)×100

Test Example 2

Tests on Controlling Effects against Silverleaf Whitefly (*Bemisia Argentifoli*)

Adults of silverleaf whitefly were released on cucumber with only one first true leaf left and other leaves cut off and planted in a pot, and permitted to lay eggs for about 8 hours. Thereafter, they were left for from 7 to 10 days in a constant temperature chamber at 25° C. with lightening. The number of hatchings was counted, and then, the infested leaf was dipped for about 10 seconds in an insecticidal solution prepared to bring the concentration of the compound of the present invention to 200 ppm or 50 ppm and dried in air. After the treatment, it was left in a constant temperature chamber at 25° C. with lightening for from 10 to 14 days, whereupon the number of old instar larvae and the number of pupae were counted, and the protective value was obtained by the following equation. The protective value at 200 ppm was obtained with respect to the above-mentioned compound Nos. 11 and 21, whereby they showed high controlling effects with a protective value of at least 80%, and the protective value at 50 ppm was obtained with respect to the above-mentioned compound Nos. 3, 9, 12, 14 to 20, 22, 38 and 39, whereby all compounds showed high controlling effects with a protective value of at least 80%.

Protective value (1)=(1−((Ta×Cb)/(Tb×Ca)))×100

Ta: The number of old instar larvae+the number of pupae after the treatment at the treated section
Tb: The number of hatchings before the treatment at the treated section
Ca: The number of old instar larvae+the number of pupae after the treatment at untreated section
Cb: the number of hatching before the treatment at the untreated section Test Example 3

Test on Controlling Effects Against Green Peach Aphid (*Myzus persicae*)

The petiole of eggplant with only one true leaf left and planted in a pot, was coated with a sticker, and then about 2-3 apterous viviparous females of green peach aphid were released on the true leaf. After two days from the release, the adult insects were removed, and the number of larvae was counted. Then, the leaf of the eggplant infested with the larvae was dipped in an insecticidal solution prepared to bring the concentration of the compound of the present invention to 800 ppm, for about 10 seconds, then dried in air and left in a constant temperature chamber at 25° C. with lightening. The number of survived insects was counted 5 days after the treatment, and the mortality was calculated by the following equation. The mortality was obtained with respect to the above-mentioned compound Nos. 2, 9, 11, 14 to 18, 20, 22, 23, 38, 39, 42 and 90, whereby all compounds showed high controlling effects with a mortality of at least 90%.

Mortality (%)=(1−(number of survived insects/number of treated insects))×100

Test Example 4

Test on Controlling Effects Against Cotton Aphid (*Aphis gossypii*)

The petiole of eggplant with only one true leaf left and planted in a pot, was coated with a sticker, and then about 3-4 apterous viviparous females of cotton aphid were released on the true leaf. After two days from the release, the adult insects were removed, and the number of larvae was counted. The leaf of eggplant infested with the larvae was dipped in an insecticidal solution is prepared to bring the concentration of the compound of the present invention to 50 ppm, for about 10 seconds, then dried in air and left in a constant temperature chamber at 25° C. with lightening. The number of survived insects was counted 5 days after the treatment, and the mortality was obtained in the same manner as in the above Test Example 3. The mortality was obtained with respect to the above-mentioned compound Nos. 16, 18 and 22, whereby all compounds showed high controlling effects with a mortality of at least 90%.

Test Example 5

Test on Controlling Effects Against Serpentine Leafminer (*Liriomyza trifolii*)

A kidney bean leaf segment having eggs of serpentine leafminer uniformly laid thereon, was dipped for about 10 seconds in an insecticidal solution prepared to bring the concentration of the compound of the present invention to 25 ppm or 12.5 ppm, and then dried in air A wet filter paper was laid in a plastic cup having a diameter of 9 cm and a height of 4 cm, and the dried kidney bean leaf segment was placed thereon. Then, after putting a cover thereon, it was left in a constant temperature chamber at 25° C. with lightening. The number of old instar larvae and the number of pupae were counted for 6 to 8 days after the treatment, and the protective value was calculated by the following equation. The protective value was obtained at 25 ppm with respect to the above-mentioned compound Nos. 9, 14 and 23, whereby all compounds showed high controlling effects with a protective value of at least 90%, and the protective value at 12.5 ppm was obtained with respect to the above-mentioned compound Nos. 2, 3, 11, 12, 15 to 18, 20 and 22, whereby all compounds showed high controlling effects with a protective value of at least 90%.

Protective value (%)=(1−((number of old instar larvae+the number of pupae at treated section)/(number of old instar larvae+number of pupae at untreated section)))×100

Test Example 6

Test on Controlling Effects Against *Thrips* palmi

From a cucumber planted in a pot, all leaves except for first true leaf were cut off. The remaining leaf was dipped for about 10 seconds in an insecticidal solution prepared to bring the concentration of the compound of the present invention to 50 ppm and dried in air. Then, a cucumber leaf segment infested with first instar larvae was placed on the above treated leaf. Next day, the cucumber leaf segment was removed, and the number of larvae moved to the treated leaf was counted. A wet filter paper was laid in a plastic cup having a diameter of 9 cm and a height of 4 cm, and the treated leaf cut off was placed thereon. Then, after putting a cover thereon, it was left in a constant temperature chamber at 25° C. with lightening. The number of survived insects was counted for 12 to 15 days after the treatment, and the protective value was obtained in the same manner as in the above Test Example 2. The protective value was obtained with respect to the above-mentioned compound Nos. 11, 12, 16, 22, 38 and 39, whereby all compounds showed high controlling effects with a protective value of at least 90%.

Test Example 7

Test on Controlling Effects Against Twenty-eight-spotted Ladybird (*Epilachna vigintioctopunctata*)

An eggplant leaf segment was dipped for about 10 seconds in an insecticidal solution prepared to bring the concentration of the compound of the present invention to 25 ppm or 12.5 ppm and dried in air. A wet filter paper was laid in a plastic cup having a diameter of 9 cm and a height of 4 cm, and the dried eggplant leaf segment was placed thereon. Five first-second instar larvae of twenty-eight-spotted ladybird were released thereon and after putting a cover thereon, left in a constant temperature chamber at 25° C. with lightening. Dead insects were counted for 4 to 6 days after the release, and the mortality was obtained in the same manner as in the above Test Example 1. Here, moribund insects were counted as dead insects. The mortality was obtained at 25 ppm with respect to the above-mentioned compound Nos. 9 and 11, whereby all compounds showed high controlling effects with a mortality of at least 90%, and the mortality was obtained at 12.5 ppm with respect to the above-mentioned compound Nos. 3, 16, 22, 38 and 39, whereby all compounds showed high controlling effects with a mortality of at least 90%.

Test Example 8

Test on Controlling Effects Against Housefly (*Musca domestics*)

10 g of a culture medium was put into a plastic cup having a diameter of 6 cm and a height of 3 cm, and then, 10 ml of an insecticidal solution prepared to bring the concentration of the compound of the present invention to 200 ppm, was added and mixed. 20 or 30 larvae at 4-day old were released, and after putting a cover thereon, it was left in a constant temperature chamber at 25° C. with lightening for from 15 to 16 days. Thereafter, the number of adults was counted, and the percent inhibition of emergence was obtained by the following equation. The percent inhibition of emergence was obtained with respect to the above-mentioned compound Nos. 3, 9, 11, 12 and 14 to 20, whereby all compounds showed high controlling effects with a percent inhibition of emergent of at least 90%.

Percent inhibition of emergence (%)=(1−(number of adults/number of released larvae))×100

Test Example 9

Test on Controlling Effects Against Formosan subterranean Termite (*Coptotermes formosanus*)

A filter paper was laid in a glass petri dish having a diameter of 9 cm, and 1 ml of an insecticidal solution prepared to bring the concentration of the compound of the present invention to 500 ppm was applied. Then, 10 workers and one soldier of Formosan subterranean termite were released, and after putting a cover, left in a constant temperature chamber at 25° C. with lightening. The number of dead workers was counted 6 days after the treatment, and the mortality was obtained by the following equation. The mortality was obtained with respect to the above compound Nos. 3, 9, 11, 12, 14 to 16 and 22, whereby all compounds showed high controlling effects with a mortality of at least 90%.

Mortality (%)=(number of dead workers/10)×100

Test Example 10

Test of Systemic Effects Against Common Cutworm (*Spodoptera litura*)

10 ml of an insecticidal solution prepared to bring the concentration of the compound of the present invention to 800 ppm or 200 ppm, was applied to the foot of cabbage at the 5th to 6th leaf stage planted in a pot. A wet filter paper was laid in a petri dish having a diameter of 9 cm, and a cabbage leaf segment cut out at ten days after the treatment was placed thereon. Ten second-third instar larvae of common cutworm were released thereon, and after putting a cover, left in a constant temperature chamber at 25° C. with lightening. Dead larvae were counted for 4 to 5 days after the release, and the mortality was obtained in the same manner as in the above Test Example 1. Here, moribund insects were counted as dead insects. The mortality at 800 ppm was obtained with respect to the above-mentioned compound No. 8 whereby it showed high controlling effects with a mortality of at least 90%, and the mortality at 200 ppm was obtained with respect to the above compound Nos. 3, 9, 11, 16, 18 and 22, whereby all compounds showed high controlling effects with a mortality of at least 90%.

Test Example 11

Test on Controlling Effects Against *Haemaphysalis longicornis*

On an inner surface of a petri dish having diameter of 9 cm, 1 ml of an acetone solution of a sample compound (concentration: 10 µg/ml) was dropwise applied by a micropipette. On the other hand, as a control section, 1 ml of acetone was dropwise applied in the same manner. The inner surface of the petri dish was dried, and then about 100 larval ticks were put, and the petri dish was covered with a polyethylene sheet and sealed with an elastic band. Thereafter, except for the observation time, the petri dish was left to stand at a constant temperature of 25° C. under a relative humidity of 100% and under a constantly dark condition. The observation was carried out every time after putting the larval ticks in the petri dish (after 5 minutes, 10 minutes, 15 minutes, 20 minutes, 30 minutes, 45 minutes, 1 hour, 2 hours, 4 hours, 6 hours and 24 hours). The number of knockdown ticks after the contact with the insecticidal compound was recorded. The foregoing operation was repeated twice.

The knockdown rate at each observation time was corrected by the following abbott correction formula. Then, a probit-time linear line was drawn, and the median knockdown time ($KT_{50}$ value) was obtained. With respect to the $KT_{50}$ values of the respective sample compounds, they were 9 minutes and 8 minutes with the above-mentioned compound No. 3, and 7.5 minutes and 6 minutes with the above-mentioned compound No. 9, while they were 80 minutes and 40 minutes with the following comparative compound A and 120 minutes and 80 minutes with the following comparative compound B.

Corrected knockdown rate (%)=[(non-knockdown rate in control section−non-knockdown rate in treated section)/non-knockdown rate in control section]× 100

Comparative compound A is the following compound which is compound 484 in WO03/24222, compound 497 in WO03/15518 and compound 2 in WO03/15519.

Comparative compound A

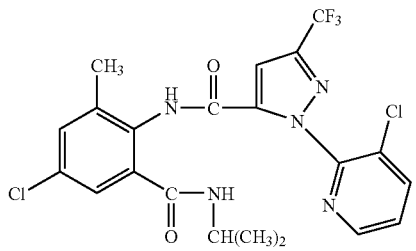

Comparative compound B is the following compound which is compound 509 in WO03/24222, compound 530 in WO03/15518 and compound 27 in WO03/15519.

Comparative compound B

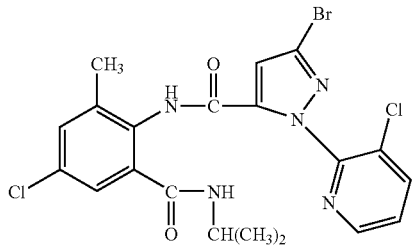

Test Example 12

Test on Controlling Effects Against Cat Flea (*Ctenocephalides felis*)

0.5 ml of an acetone solution of the compound of the present invention prepared to be 5.3 ppm was dropped in a glass tube having a flat bottom (inner diameter: 2.6 cm, bottom area: 5.3 cm$^2$, height 12 cm). The acetone was evaporated at room temperature to have a dry film containing the compound of the present invention formed on the bottom surface Ten adults of cat flea (not-yet-blood-sucked adults within five days after adult emergence) were put therein and exposed to the compound of the present invention. The test was carried out continuously three times.

Dead cat flea were counted 48 hours after the exposure and the mortality was obtained in the same manner as in the above Test Example 1. The mortality was obtained with respect to the above-mentioned compound No. 16, whereby it showed high controlling effects with a mortality of at least 90%.

Formulation Example 1

| | |
|---|---|
| (1) Compound of the present invention | 20 parts by weight |
| (2) Clay | 72 parts by weight |
| (3) Sodium lignin sulfonate | 8 parts by weight |

The above components are uniformly mixed to obtain a wettable powder.

Formulation Example 2

| | |
|---|---|
| (1) Compound of the present invention | 5 parts by weight |
| (2) Talc | 95 parts by weight |

The above components are uniformly mixed to obtain a dust.

Formulation Example 3

| | |
|---|---|
| (1) Compound of the present invention | 20 parts by weight |
| (2) N,N'-dimethylacetamide | 20 parts by weight |
| (3) Polyoxyethylenealkylphenyl ether | 10 parts by weight |
| (4) Xylene | 50 parts by weight |

The above components are uniformly mixed and dissolved to obtain an emulsifiable concentrate.

Formulation Example 4

| | |
|---|---|
| (1) Clay | 68 parts by weight |
| (2) Sodium lignin sulfonate | 2 parts by weight |
| (3) Polyoxyethylenealkylaryl sulfate | 5 parts by weight |
| (4) Fine silica powder | 25 parts by weight |

A mixture of the above components is mixed with compound of the present invention in a weight ratio of 4:1 to obtain a wettable powder.

Formulation Example 5

| | |
|---|---|
| (1) Compound of the present invention | 50 parts by weight |
| (2) Oxylated polyalkylphenyl phosphate-triethanolamine | 2 parts by weight |
| (3) Silicone | 0.2 part by weight |
| (4) Water | 47.8 parts by weight |

The above components are uniformly mixed and pulverized to obtain a base liquid, and
(5) Sodium polycarboxylate 5 parts by weight
(6) Anhydrous sodium sulfate 42.8 parts by weight are added, and the mixture is uniformly mixed, granulated and dried to obtain water-dispersible granules Formulation Example 6

| | |
|---|---|
| (1) Compound of the present invention | 5 parts by weight |
| (2) Polyoxyethyleneoctylphenyl ether | 1 part by weight |
| (3) polyoxyethylene phosphoric acid ester | 0.1 part by weight |
| (4) Granular calcium carbonate | 93.9 parts by weight |

The above components (1) to (3) are preliminarily uniformly mixed and diluted with a proper amount of acetone, and then the mixture is sprayed onto the component (4), and acetone is removed to obtain granules Formulation Example 7

| | |
|---|---|
| (1) Compound of the present invention | 2.5 parts by weight |
| (2) N-methyl-2-pyrrolidone | 2.5 parts by weight |
| (3) Soybean oil | 95.0 parts by weight |

The above components are uniformly mixed and dissolved to obtain an ultra low volume formulation.

Formulation Example 8

| | |
|---|---|
| (1) Compound of the present invention | 40 parts by weight |
| (2) Oxylated polyalkylphenylphosphate-triethanolamine | 2 parts by weight |
| (3) Silicone | 0.2 part by weight |
| (4) Zanthan gum | 0.1 part by weight |
| (5) Ethylene glycol | 5 parts by weight |
| (6) Water | 52.7 parts by weight |

The above components are uniformly mixed and pulverized to obtain a water-based suspension concentrate.

Formulation Example 9

| | |
|---|---|
| (1) Compound of the present invention | 10 parts by weight |
| (2) Diethylene glycol monoethyl ether | 90 parts by weight |

The above components are uniformly mixed to obtain a soluble concentrate.

The entire disclosures of Japanese Patent Application No. 2004-041295 filed on Feb. 18, 2004, Japanese Patent Application No 2004-133722 filed on Apr. 28, 2004, Japanese Patent Application No. 2004-261507 filed on Sep. 8, 2004 and Japanese Patent Application No. 2004-295778 filed on Oct. 8, 2004 including specifications, claims and summaries are incorporated herein by reference in their entireties.

What is claimed is:

1. An insecticidal, miticidal, or nematicidal composition, wherein the composition comprises at least one agricultural adjuvant and at least one active ingredient selected from N-[4-chloro-2-methyl-6-[[α-methyl-(cyclopropylmethy)amino]carbonyl]-phenyl]-3-(trifluoromethyl)-1-(3-chloro-2-pyridyl)-1H-pyrazole-5-carboxamide, N-[4-chloro-2-methyl-6-[[α-methyl-(cyclopropyl-methy)amino]carbonyl]-phenyl]-3-bromo-1-(3-chloro-2-pyridyl)-1H-pyrazole-5-carboxamide, N-[2-bromo-4-chloro-6-[[α-methyl-(cyclopropylmethy)amino]carbonyl]-phenyl]-3-bromo-1-(3-chloro-2-pyridyl )-1H-pyrazole-5-carboxamide, and salts thereof.

2. A pesticidal composition, wherein the composition is effective against at least one of animal parasitic acarina and flea and comprises at least one agricultural adjuvant and at least one active ingredient selected from N-[4-chloro-2-methyl-6-[[α-methyl-(cyclopropylmethyl)amino]-carbonyl ]-phenyl]-3-(trifluoromethyl)-1-(3-chloro-2-pyridyl)-1H-pyrazole-5-carboxamide, N-[4-chloro-2-methyl-6-[[-methyl-(cyclopropylmethy)amino]carbonyl]-phenyl]-3-bromo-1-(3-chloro-2-pyridyl)-1H-pyrazole-5-carboxamide, N[2-bromo-4-chloro-6-[[α-methyl-(cyclopropylmethyl)-amino] carbonyl]-phenyl]-3-bromo-1-(3-chloro-2-pyridyl)-1H-pyrazole-5-carboxamide, and salts thereof.

3. A method for controlling insects or mites, wherein the method comprises applying an effective amount for controlling insects or mites of at least one compound selected from N-[4-chloro-2-methyl-6-[[α-methyl-(cyclopropylmethy)amino]carbonyl]-phenyl]-3-(trifluoromethyl)-1-(3-chloro-2-pyridyl)-1H-pyrazole-5-carboxamide, N-[4-chloro-2-methyl-6-[[α-methyl-(cyclopropyl-methy)amino]carbonyl]-phenyl]-3-bromo-1-(3-chloro-2-pyridyl)-1H-pyrazole-5-carboxamide, N-[2-bromo-4-chloro-6-[[α-methyl-(cyclopropylmethyl)-amino]carbonyl]-phenyl]-3-bromo-1-(3-chloro-2-pyridyl)-1H-pyrazole-5-carboxamide, and salts thereof.

4. A method for controlling animal parasitic acarina or flea, wherein the method comprises applying an effective amount for controlling animal parasitic acarina or flea of at least one compound selected from N-[4-chloro-2-methyl-6-[[α-methyl-(cyclopropylmethyl)amino]carbonyl]-phenyl]-3-(trifluoromethyl)-1-(3-chloro-2-pyridyl)-1H-pyrazole-5-carboxamide, N-[4-chloro-2-methyl-6-[[α-methyl-(cyclopropylmethy)amino]carbonyl]-phenyl]-3-bromo-1-(3-chloro-2-pyridyl)-1H-pyrazole-5-carboxamide, N-[2-bromo-4-chloro-6-[[α-methyl-(cyclopropylmethy)amino]-carbonyl]-phenyl]-3-bromo-1-(3-chloro-2-pyridyl)-1H-pyrazole-5-carboxamide, and salts thereof.

* * * * *

UNITED STATES PATENT AND TRADEMARK OFFICE
CERTIFICATE OF CORRECTION

PATENT NO. : 7,994,201 B2  
APPLICATION NO. : 12/552077  
DATED : August 9, 2011  
INVENTOR(S) : T. Koyanagi et al.

Page 1 of 1

It is certified that error appears in the above-identified patent and that said Letters Patent is hereby corrected as shown below:

At column 30, line 12 (claim 1, line 4) of the printed patent,
"(cyclopropylmethy)" should be -- (cyclopropylmethyl) --.

At column 30, line 18 (claim 1, line 10) of the printed patent,
"(cyclopropylmethy)" should be -- (cyclopropylmethyl) --.

At column 30, line 28 (claim 2, line 8) of the printed patent,
"(cyclopropylmethy)" should be -- (cyclopropylmethyl) --.

At column 30, line 36 (claim 3, line 4) of the printed patent,
"(cyclopropylmethy)" should be -- (cyclopropylmethyl) --.

At column 30, line 39 (claim 3, line 7) of the printed patent,
"(cyclopropyl-methy)" should be -- (cyclopropylmethyl) --.

At column 30, line 52 (claim 4, line 8) of the printed patent,
"(cyclopropylmethy)" should be -- (cyclopropylmethyl) --.

At column 30, line 52 (claim 4, line 8) of the printed patent,
"(cyclopropylmethy)" should be -- (cyclopropylmethyl) --.

At column 30, line 54 (claim 4, line 10) of the printed patent,
"(cyclopropylmethy)" should be -- (cyclopropylmethyl) --.

Signed and Sealed this  
Third Day of April, 2012

David J. Kappos  
*Director of the United States Patent and Trademark Office*